US012661714B2

(12) United States Patent
Akamatsu et al.

(10) Patent No.: US 12,661,714 B2
(45) Date of Patent: Jun. 23, 2026

(54) STORAGE FOR POWDER MATERIAL FOR METAL 3D PRINTER, AND METHOD FOR STORING POWDER MATERIAL FOR METAL 3D PRINTER

(71) Applicant: TAIYO NIPPON SANSO CORPORATION, Tokyo (JP)

(72) Inventors: Ryo Akamatsu, Tokyo (JP); Tomohiro Oyama, Tokyo (JP); Junichiro Asai, Tokyo (JP); Kan Murayama, Tokyo (JP)

(73) Assignee: TAIYO NIPPON SANSO CORPORATION, Tokyo (JP)

( * ) Notice: Subject to any disclaimer, the term of this patent is extended or adjusted under 35 U.S.C. 154(b) by 0 days.

(21) Appl. No.: 18/877,155

(22) PCT Filed: Jun. 12, 2023

(86) PCT No.: PCT/JP2023/021762
§ 371 (c)(1),
(2) Date: Dec. 19, 2024

(87) PCT Pub. No.: WO2023/248852
PCT Pub. Date: Dec. 28, 2023

(65) Prior Publication Data
US 2026/0001139 A1 Jan. 1, 2026

(30) Foreign Application Priority Data
Jun. 24, 2022 (JP) ................................. 2022-101704

(51) Int. Cl.
*B22F 12/50* (2021.01)
*B33Y 40/00* (2020.01)
(Continued)

(52) U.S. Cl.
CPC .............. *B22F 12/50* (2021.01); *B33Y 40/00* (2014.12); *B33Y 50/00* (2014.12); *G01N 33/0011* (2013.01)

(58) Field of Classification Search
None
See application file for complete search history.

(56) References Cited

U.S. PATENT DOCUMENTS

2019/0176404 A1 6/2019 Schoeneborn et al.

FOREIGN PATENT DOCUMENTS

CN 110854038 A 2/2020
CN 210880928 U 6/2020
(Continued)

OTHER PUBLICATIONS

Office Action for Japanese Application No. 2022-101704 dated Oct. 25, 2022, 5 pages (with English Translation).
(Continued)

*Primary Examiner* — Anthony M Liang
(74) *Attorney, Agent, or Firm* — Nixon & Vanderhye P.C.

(57) ABSTRACT

A storage for powder material for a metal 3D printer comprising a storage main body having a sealed space inside and capable of placing one or more storage containers for storing powder material for a metal 3D printer in the sealed space, a purge gas supply path for supplying a purge gas made from air to the sealed space, and an oxygen/moisture removal device for removing oxygen and moisture from the air which is located in the purge gas supply path. This storage can provide a storage environment suitable for powder material for a metal 3D printer without being restricted by installation location.

20 Claims, 3 Drawing Sheets

(51) Int. Cl.
   *B33Y 50/00* (2015.01)
   *G01N 33/00* (2006.01)

(56) References Cited

FOREIGN PATENT DOCUMENTS

| | | | |
|---|---|---|---|
| CN | 112930416 | A | 6/2021 |
| CN | 216780330 | U | 6/2022 |
| JP | H0633813 | U | 5/1994 |
| JP | 2001500669 | A | 1/2001 |
| JP | 2002274608 | A | 9/2002 |
| JP | 2007-281083 | A | 10/2007 |
| JP | 2021130870 | A * | 9/2021 |
| KR | 10-1998-0027353 | A | 7/1998 |
| KR | 10-2010-0011824 | A | 2/2010 |

OTHER PUBLICATIONS

International Search Report for PCT/JP2023/021762 dated Aug. 15, 2023, 5 pages.
Written Opinion of the ISA for PCT/JP2023/021762 dated Aug. 15, 2023, 4 pages.
Notification of the First Office Action mailed Mar. 29, 2025 in Chinese Application No. 202380045476.4, with English translation, 27 pages.
Extended European Search Report dated Oct. 29, 2025 issued in European Application No. 23827038.3 (15 pages).
Decision of Grant mailed May 23, 2023 (drafted May 17, 2023) in Japanese Application No. 2022-101704, with English translation, 5 pages.
Notice of Reasons for Refusal mailed Feb. 14, 2023 (drafted Feb. 10, 2023) in Japanese Application No. 2022-101704, with English translation, 4 pages.

\* cited by examiner

STORAGE FOR POWDER MATERIAL FOR METAL 3D PRINTER, AND METHOD FOR STORING POWDER MATERIAL FOR METAL 3D PRINTER

CROSS-REFERENCE TO RELATED APPLICATIONS

This application is the U.S. national phase of International Application No. PCT/JP2023/021762 filed Jun. 12, 2023 which designated the U.S. and claims priority to Japanese Patent Application No. 2022-101704 filed Jun. 24, 2022, the entire contents of each of which are hereby incorporated by reference.

TECHNICAL FIELD

The present invention relates to a storage for powder material for a metal 3D printer, and a method for storing powder material for a metal 3D printer.

BACKGROUND ART

Additive manufacturing is capable of producing structures of any shape in a short period of time, and is therefore attracting attention as a promising technology in advanced technology fields such as the aircraft industry and medical care.

As an example of a manufacturing device that uses additive manufacturing technology, a metal 3D printer is known that sinters raw powder material made of metal stored in a modeling stage using a laser or the like. Metal 3D printers can precisely manufacture metal objects by stacking sintered metal layers one after another on the modeling stage.

Examples of raw powders used in metal 3D printers (hereinafter sometimes simply referred to as "powder material for a metal 3D printer") include aluminum alloys, titanium alloys, iron-based alloys, nickel-based alloys, and high-entropy alloys. These raw powders are stored in a storage container, but when stored in the air, most metals oxidize due to oxygen in the air. When oxidized raw powder is used, the amount of oxygen dissolved in the molded object increases, affecting the molding characteristics. In addition, the storage container has low moisture-proofing performance, and the raw powder absorbs moisture until it becomes the same as in the air in a few days. For example, when raw powder made of an aluminum alloy is used, if moisture is present during the molding of the metal layer, deformation occurs in the molded object after the heat treatment process. In addition, when raw powder made of a titanium alloy is used, if oxygen or moisture is present during the molding of the metal layer, the mechanical properties of the molded object deteriorate.

As described above, the storage environment is important for powder material for a metal 3D printer because oxygen and moisture adhering to the raw powder material have an effect when forming a metal layer. Therefore, it is preferable to store powder material for a metal 3D printer in a storage that can remove oxygen and moisture.

A known example of a storage capable of removing oxygen and moisture is disclosed in Patent Document 1. Patent Document 1 discloses a technology that uses an inert gas such as nitrogen gas, helium gas, or argon gas as a purge gas and adjusts the moisture concentration and the oxygen concentration in the storage to provide a storage environment suitable for powder material for a metal 3D printer.

PRIOR ART DOCUMENTS

Patent Documents

Patent Document 1 Japanese Unexamined Patent Application, First Publication No. 2021-130870

SUMMARY OF INVENTION

Problem to be Solved by the Invention

However, the storage disclosed in Patent Document 1 uses an inert gas such as nitrogen gas, helium gas, or argon gas as a purge gas, and therefore requires inert gas supply equipment and supply capacity, which poses the problem that the installation location of the storage is limited.

The present invention has been made in consideration of the above circumstances, and has an object to provide a storage for powder material for a metal 3D printer that is capable of providing a storage environment suitable for powder material for a metal 3D printer without being restricted by installation location, and a method for storing powder material for a metal 3D printer.

Means for Solving the Problem

In order to solve the above problems, the present invention has the following configurations.

[1] A storage for powder material for a metal 3D printer, including:

a storage main body having a sealed space inside and capable of placing one or more storage containers for storing powder material for a metal 3D printer in the sealed space;

a purge gas supply path for supplying a purge gas made from air to the sealed space; and an oxygen/moisture removal device for removing oxygen and moisture from the air which is located in the purge gas supply path.

[2] The storage for powder material for a metal 3D printer according to [1], wherein the oxygen/moisture removal device is a gas separation membrane or a filled cylinder filled with a gas adsorbent.

[3] The storage for powder material for a metal 3D printer according to [1] or [2], wherein the storage further includes:

a first on-off valve located on the primary side of the oxygen/moisture removal device in the purge gas supply path;

a first flow rate regulator located on the secondary side of the oxygen/moisture removal device in the purge gas supply path;

a bypass path branching off from the purge gas supply path on the primary side of the first on-off valve and merging with the purge gas supply path on the secondary side of the first flow rate regulator;

a second on-off valve located in the bypass path;

a second flow rate regulator located in the bypass path;

an oxygen concentration measuring device measuring an oxygen concentration in the sealed space;

a moisture concentration measuring device measuring a moisture concentration in the sealed space; and a control device capable of transmitting and receiving signals to and from the first on-off valve, the first flow rate regulator, the second on-off valve, the second flow rate regulator, the oxygen concentration-measuring device, and the moisture concentration-measuring device.

[4] The storage for powder material for a metal 3D printer according to any one of [1] to [3], wherein the storage further includes:

a heater for heating the sealed space, and a temperature-measuring device for measuring a temperature of the sealed space.

[5] The storage for powder material for a metal 3D printer according to [4], wherein an outlet of the purge gas supply path opens at the bottom of the sealed space.

[6] The storage for powder material for a metal 3D printer according to any one of [3] to [5], wherein the storage further includes an exhaust path for exhausting atmospheric gas in the sealed space to the outside of the storage main body as exhaust gas, and wherein at least one of the oxygen concentration measuring device and the moisture concentration measuring device are positioned in the exhaust path.

[7] The storage for powder material for a metal 3D printer according to any one of [1] to [6], wherein the storage further includes:

a third on-off valve located on the secondary side of the oxygen/moisture removal device in the purge gas supply path, and an exhaust path branching off from the purge gas supply path on the secondary side of the oxygen/moisture removal device and the primary side of the third on-off valve.

[8] A method for storing powder material for a metal 3D printer, including:

placing one or more storage containers for storing powder material for a metal 3D printer in a sealed space, and supplying a purge gas, which is made from air and obtained by removing oxygen from the air, to the sealed space.

[9] The method for storing powder material for a metal 3D printer according to [8], wherein the supply of the purge gas is stopped after the moisture concentration and the oxygen concentration in the sealed space fall below required threshold values.

[10] The method for storing powder material for a metal 3D printer according to [9], wherein after the supply of the purge gas is stopped, the purge gas is supplied to the sealed space every required time, and the moisture concentration and the oxygen concentration in the sealed space are measured.

[11] The method for storing powder material for a metal 3D printer according to [10], wherein the supply of the purge gas is resumed when at least one of the moisture concentration and the oxygen concentration in the sealed space exceeds a threshold value.

[12] The method for storing powder material for a metal 3D printer according to any one of [8] to [11], wherein a temperature of the sealed space is set to a required temperature.

[13] The method for storing powder material for a metal 3D printer according to any one of [8] to [12], wherein the oxygen concentration in the sealed space is maintained at 3% by volume or less, and a dew point temperature of the sealed space is maintained at −40° C. or less.

[14] A storage for powder material for a metal 3D printer including:

a storage main body having a sealed space inside and capable of placing one or more storage containers for storing powder material for a metal 3D printer in the sealed space;

a purge gas supply path for supplying a purge gas made from air to the sealed space; and an oxygen/moisture removal device for removing oxygen and moisture from the air which is located in the purge gas supply path;

a first on-off valve located on the primary side of the oxygen/moisture removal device in the purge gas supply path;

a first flow rate regulator located on the secondary side of the oxygen/moisture removal device in the purge gas supply path;

a bypass path branching off from the purge gas supply path on the primary side of the first on-off valve and merging with the purge gas supply path on the secondary side of the first flow rate regulator;

a second on-off valve located in the bypass path;

a second flow rate regulator located in the bypass path;

an oxygen concentration measuring device for measuring an oxygen concentration in the sealed space;

a moisture concentration measuring device for measuring a moisture concentration in the sealed space; and a control device capable of transmitting and receiving signals to and from the first on-off valve, the first flow rate regulator, the second on-off valve, the second flow rate regulator, the oxygen concentration measuring device, and the moisture concentration measuring device.

[15] A storage for powder material for a metal 3D printer, including:

a storage main body having a sealed space inside and capable of placing one or more storage containers for storing powder material for a metal 3D printer in the sealed space;

a purge gas supply path for supplying a purge gas made from air to the sealed space;

an oxygen/moisture removal device for removing oxygen and moisture from the air which is located in the purge gas supply path;

a third on-off valve located on the secondary side of the oxygen/moisture removal device in the purge gas supply path; and an exhaust path that branches off from the purge gas supply path on the secondary side of the oxygen/moisture removal device and on the primary side of the third on-off valve and has an on-off valve.

[16] A storage for powder material for a metal 3D printer, including:

a storage main body having a sealed space inside and capable of placing one or more storage containers for storing powder material for a metal 3D printer in the sealed space;

a purge gas supply path for supplying a purge gas made from air to the sealed space;

an oxygen/moisture removal device for removing oxygen and moisture from the air which is located in the purge gas supply path;

a third on-off valve located on the secondary side of the oxygen/moisture removal device in the purge gas supply path;

an exhaust path branching off from the purge gas supply path on the secondary side of the oxygen/moisture removal device and on the primary side of the third on-off valve;

a first on-off valve located on the primary side of the oxygen/moisture removal device in the purge gas supply path;

a first flow rate regulator located on the secondary side of the oxygen/moisture removal device in the purge gas supply path;

a bypass path branching off from the purge gas supply path on the primary side of the first on-off valve and merging with the purge gas supply path on the secondary side of the first flow rate regulator;

a second on-off valve located in the bypass path;

a second flow rate regulator located in the bypass path;

an oxygen concentration measuring device for measuring an oxygen concentration in the sealed space;

a moisture concentration measuring device for measuring a moisture concentration in the sealed space; and a control device capable of transmitting and receiving signals to and from the first on-off valve, the first flow rate regulator, the second on-off valve, the second flow rate regulator, the oxygen concentration measuring device, and the moisture concentration measuring device.

[17] The storage for powder material for a metal 3D printer according to any one of to [16], wherein the oxygen/moisture removal device is a gas separation membrane or a packed cylinder filled with a gas adsorbent.

[18] The storage for powder material for a metal 3D printer according to any one of to [16], wherein the storage further includes:

a heater for heating the sealed space, and a temperature measuring device for measuring a temperature of the sealed space.

[19] The storage for powder material for a metal 3D printer according to [18], wherein an outlet of the purge gas supply path opens at the bottom of the sealed space.

[20] The storage for powder material for a metal 3D printer according to any one of or [16], wherein the storage further includes:

an exhaust path for exhausting atmospheric gas in the sealed space to the outside of the storage main body as exhaust gas, and at least one of the oxygen concentration measuring device and the moisture concentration measuring device are positioned in the exhaust path.

[21] A method for storing powder material for a metal 3D printer using the storage for powder material for a metal 3D printer according to any one of to [16], including:

placing one or more storage containers for storing the powder material for a metal 3D printer in a sealed space inside the storage main body; and supplying a purge gas, which is made from air and obtained by removing oxygen and moisture from the air, to the sealed space.

[22] The method for storing powder material for a metal 3D printer according to [21], wherein the supply of the purge gas is stopped after the moisture concentration and the oxygen concentration in the sealed space fall below required threshold values.

[23] The method for storing powder material for a metal 3D printer according to [22], wherein after the supply of the purge gas is stopped, the purge gas is supplied to the sealed space every required time, and the moisture concentration and the oxygen concentration in the sealed space are measured.

[24] The method for storing powder material for a metal 3D printer according to [23], wherein the supply of the purge gas is resumed when at least one of the moisture concentration and the oxygen concentration in the sealed space exceeds a threshold value.

[25] The method for storing powder material for a metal 3D printer according to any one of to [24], wherein a temperature of the sealed space is set to a required temperature.

[26] The method for storing powder material for a metal 3D printer according to any one of to [25], wherein the oxygen concentration in the sealed space is maintained at 3% by volume or less, and a dew point temperature of the sealed space is maintained at $-40°$ C. or less.

Effects of the Invention

According to the storage for powder material for a metal 3D printer and the method for storing powder material for a metal 3D printer of the present invention, a storage environment suitable for powder material for a metal 3D printer can be provided without being restricted by the installation location.

DETAILED DESCRIPTION OF THE PREFERRED EMBODIMENTS

Hereinafter, a storage for powder material for a metal 3D printer, which is an embodiment according to the present invention, will be described in detail with reference to the drawings, together with a method for storing powder material for a metal 3D printer using the storage for powder material for a metal 3D printer. Note that the figures used in the following description may show characteristic parts in an enlarged scale for the sake of convenience in order to make the characteristics easier to understand, and the dimensional ratios of each component may not necessarily be the same as the actual ones.

Storage for Powder Material for Metal 3D Printer

Figure 1:
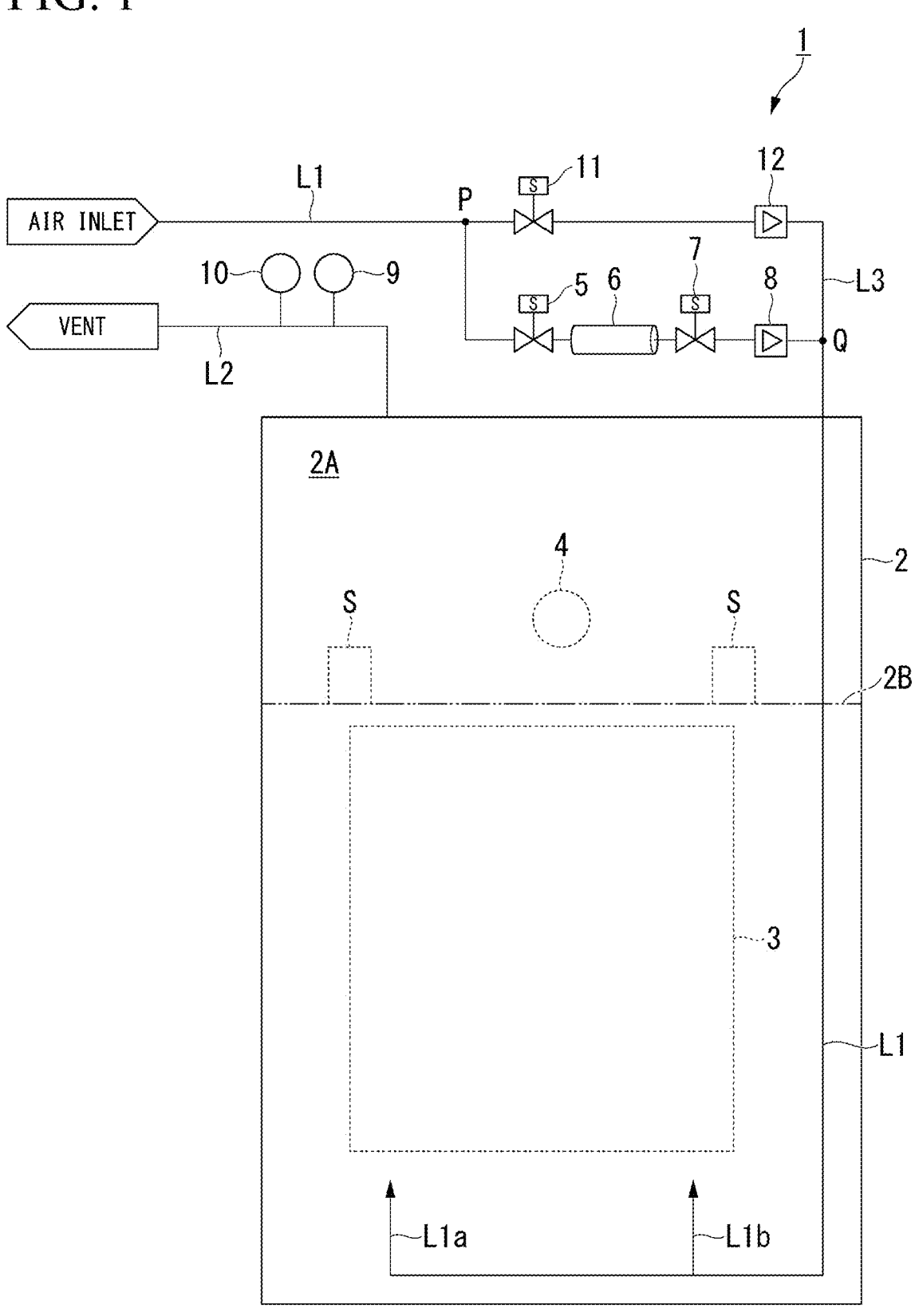
FIG. 1 is a schematic diagram showing an embodiment of the configuration of a storage for powder material for a metal 3D printer according to the present invention.
Figure 2:
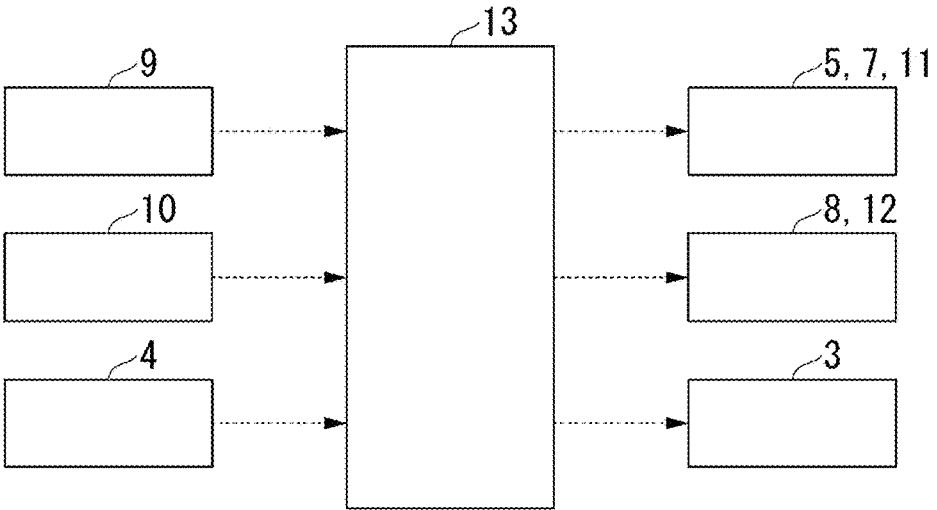
FIG. 2 is a diagram showing an embodiment of the configuration of a control device applicable to the storage for powder material for a metal 3D printer according to the present invention.

First, the configuration of a storage for powder material for a metal 3D printer, which is one embodiment according to the present invention, will be described. FIG. 1 is a schematic diagram showing an embodiment of the configuration of a storage for powder material for a metal 3D printer according to the present invention. FIG. 2 is a diagram showing an embodiment of the configuration of a control device applicable to the storage for powder material for a metal 3D printer according to the present invention.

As shown in FIGS. 1 and 2, a storage for powder material for a metal 3D printer (hereinafter, sometimes simply referred to as "storage") 1 of the present embodiment mainly includes a cabinet (storage main body) 2, a heater (heating device) 3, a temperature measuring device 4, a purge gas supply path L1, an exhaust path L2, a bypass path L3, an on-off valve (first on-off valve) 5, an oxygen/moisture removal device 6, an on-off valve (third on-off valve) 7, a flow rate regulator (first flow rate regulator) 8, an oxygen concentration measuring device 9, a moisture concentration measuring device 10, an on-off valve (second on-off valve) 11, a flow rate regulator (second flow rate regulator) 12, and a control device 13.

As shown in FIG. 1, the storage 1 of the present embodiment stores raw powder material for a metal 3D printer (hereinafter, may be simply referred to as "raw powder") in an environment maintained at appropriate oxygen and moisture concentrations. When modeling with the metal 3D printer, the raw powder is taken out from the storage 1 and used.

The raw powder to be stored is not particularly limited as long as it can be used in metal 3D printers. Examples of such raw powder include aluminum alloys, titanium alloys, iron-based alloys, nickel-based alloys, and high-entropy alloys.

The raw powder is stored and preserved in a storage container S. Here, the storage container S is made of resin or metal and is composed of a container body and a lid. The raw powder may be stored in the container body and stored with the lid on or without the lid on.

The cabinet (storage main body) 2 is a rectangular storage having a sealed space 2A inside. The structure of the cabinet 2 is not particularly limited. The cabinet 2 may have a back panel, a top panel, a bottom panel, a pair of side panels, and an opening/closing door. The sealed space 2A is provided with a plurality of shelves 2B (only one is shown in FIG. 1) having different heights in the vertical direction, and the sealed space 2A is divided by the plurality of shelves 2B. The cabinet 2 can place one or more storage containers S for storing the raw powder on each shelf 2B.

There are no particular limitations on the door, as long as it can form an opening that allows the storage container S containing the raw powder to be inserted into and removed from the sealed space 2A. Examples of the doors include single-sided doors, double doors, sliding doors, and the like.

The opening and closing door is preferably sealed so that, when closed, oxygen and moisture are not transmitted into the environment in which the storage 1 is installed in the sealed space 2A.

In addition, it is preferable to provide a sensor on the door so that a signal is sent when the door is opened.

The capacity of the cabinet 2 (in other words, the volume of the sealed space 2A) is not particularly limited and can be appropriately selected depending on the storage amount of the storage containers S. The capacity of the cabinet 2 can be 100 to 2000 L, and from the viewpoint of practicality and the ease of carrying in and out the powder containers, it is preferably 300 to 1500 L, and more preferably 600 to 1200 L.

The material of the cabinet 2 is not particularly limited as long as it has a heat insulating and heat retaining effect. Examples of the material of the cabinet 2 include iron-based materials and resinous materials. Among these, from the viewpoint of load resistance and conductivity, it is preferable to use a laminated structure of a metal plate such as stainless steel or steel and a heat insulating material such as urethane resin.

The heater (heating device) 3 heats the sealed space 2A of the cabinet 2 to a required temperature or keeps it at a required temperature. The heater 3 is located on the entire surface of the back panel. The position where the heater 3 is provided is not particularly limited as long as it faces the sealed space 2A. Examples of such positions include the top panel, the bottom panel, a pair of side surfaces, and an opening/closing door (not shown). The heater 3 may be provided in two or more places, such as the back panel and a pair of side surfaces, or may be provided only on a part of the back panel rather than on the entire surface.

The heater 3 is not particularly limited as long as it can heat the sealed space 2A to a required temperature or keep it at a required temperature. Examples of the heater 3 include a rubber heater and a sheath-type heater. Among these, it is preferable to use a rubber heater from the viewpoint of ease of attachment to the back panel and the safety of the operator.

It is preferable to provide a heater cover (contact prevention plate) on the surface of the heater 3. This makes it possible to prevent an operator from accidentally touching the heater 3 directly when placing the storage container S in the storage 1 or removing the storage container S from the storage 1.

As shown in FIG. 1, the temperature measuring device 4 is disposed in the cabinet 2 in order to measure the temperature of the sealed space 2A. Specifically, the temperature measuring device 4 is disposed near the placement surface of the shelf 2B. The number of temperature measuring devices 4 is not particularly limited. By disposing a plurality of temperature measuring devices 4 in the cabinet 2, the temperature distribution in the sealed space 2A can be measured. This allows the temperature distribution in the sealed space 2A to be appropriately adjusted.

There is no particular limitation on the temperature measuring device 4 as long as it can measure the temperature of the sealed space 2A. For example, the temperature measuring device 4 may be a K-sheath thermocouple manufactured by Yamazato Sangyo Co., Ltd.

As shown in FIG. 2, the heater 3 and the temperature measuring device 4 are connected to the control device 13 by a wired or wireless signal line. This allows the control device 13 to receive the measured temperature value of the sealed space 2A from the temperature measuring device 4 as an electric signal, and to transmit a control signal to the heater 3 for heating or keeping the sealed space 2A warm based on the received measured values.

As shown in FIG. 1, the purge gas supply path L1 is a gas supply pipe that supplies a purge gas into the sealed space 2A inside the cabinet 2.

The storage 1 of the present embodiment uses a purge gas made from air as a raw material. In other words, the storage 1 of the present embodiment uses air as a raw material for the purge gas.

The raw air is preferably compressed air which is pressurized by an air compressor (air compression device). The raw air is preferably dry air (dried air) from which moisture has been removed. Furthermore, the raw air is preferably high-purity air (clean air) from which minute impurities (particles) have been removed.

Specifically, when a gas separation membrane module is used as the oxygen/moisture removal device 6 described later, it is preferable to use clean dry air (CDA) as the raw air. This removes particles contained in the raw air, suppressing deterioration in the performance of the gas separation membrane and allowing the gas separation membrane module to be used for a long period of time. Furthermore, since the moisture concentration of the raw air is low, the moisture concentration of the purge gas (inert gas) obtained from the gas separation membrane module can be reduced.

The purge gas supply path L1 has outlets L1a, L1b that open below the sealed space 2A.

The outlets L1a, L1b are arranged at a predetermined distance below (near the bottom) the sealed space 2A. By introducing the purge gas from near the bottom of the sealed space 2A, the aubospheric gas in the sealed space 2A can be caused to circulate from the bottom to the top. In other words, the atmospheric gas in the sealed space 2A can be stirred.

The outlets L1a and L1b are adjusted in a direction such that the blown purge gas hits the heater 3 arranged on the back panel. By blowing the purge gas against the heater 3, the heated purge gas can be supplied to the sealed space 2A.

In the purge gas supply path L1, on the secondary side of a branch point P and on the primary side of a junction point Q, the on-off valve (first on-off valve) 5, the oxygen/moisture removal device 6, the on-off valve (third on-off valve) 7, and the flow rate regulator (first flow rate regulator) 8 are located in this order.

The on-off valve (first on-off valve) 5 is located on the primary side of the oxygen/moisture removal device 6 in the purge gas supply path L1, and selects an open or closed state of the flow path of the purge gas supply path L1. By opening the on-off valve 5, the raw air can be supplied to the oxygen/moisture removal device 6 on the secondary side of the on-off valve 5. On the other hand, by closing the on-off valve 5, the supply of the raw air to the secondary side of the on-off valve 5 can be stopped. The on-off valve 5 is not particularly limited as long as it can select the open or closed state of the flow path. For example, a solenoid valve can be used as the on-off valve 5.

The oxygen/moisture removal device 6 is located in the purge gas supply path L1, and outputs nitrogen gas obtained by removing oxygen and moisture from the introduced raw air as the purge gas. In other words, the oxygen/moisture remover 6 is a device for producing the purge gas using air as a raw material.

The oxygen/moisture removal device 6 is not particularly limited as long as it can remove oxygen and moisture from the raw air. Examples of the oxygen/moisture removal device 6 include a gas separation membrane module having a gas separation membrane and a packed cylinder filled with a gas adsorbent. Among these, a gas separation membrane module and a packed cylinder filled with a gas adsorbent that can remove oxygen from raw air without using a power source are preferred. The oxygen/moisture removal device 6 may be configured by combining the gas separation membrane module in the front stage and the packed cylinder filled with a gas adsorbent in the rear stage.

Examples of gas separation membranes include polyimide resin hollow fiber membranes and carbon membranes.

An example of the gas separation membrane module having the above-mentioned gas separation membrane is the "NM-C07F" manufactured by Ube Industries, Ltd.

Examples of oxygen gas adsorbents include potassium permanganate, Cu—Zu-based gas adsorbents, and Mn-based gas adsorbents, and specific examples thereof include "N-112" manufactured by JOC Catalysts, Ltd., and "Ni3288E" manufactured by NE Chemcat Corp. Examples of moisture gas adsorbents include silica gel, and specific examples thereof include "NKHD24" manufactured by Sumika Alchem Co., Ltd., and "Zeolum F9, Zeolum F9HA, and Zeolum A3" manufactured by Tosoh Corporation.

From the viewpoint of suppressing oxidation of the raw powder, the purge gas derived from the oxygen/moisture removal device 6 preferably has a low oxygen content and moisture content (low oxygen concentration and dew point temperature). Specifically, the oxygen concentration of the purge gas is preferably 3% by volume or less, and more preferably 1% by volume or less. As the purge gas used in the storage 1 of the present embodiment, nitrogen gas having an oxygen concentration of 3% by volume or less is preferable. The dew point temperature of the purge gas is preferably $-50°$ C. or less, and more preferably $-60°$ C. or less. As the purge gas used in the storage 1 of the present embodiment, nitrogen gas having a dew point temperature of $-50°$ C. or less is preferable.

The on-off valve (third on-off valve) 7 is located on the secondary side of the oxygen/moisture removal device 6 in the purge gas supply path L1, and selects an open state or a closed state of the flow path of the purge gas supply path L1. By opening the on-off valve 7, the purge gas can be supplied to the purge gas supply path L1 on the secondary side of the on-off valve 7. On the other hand, by closing the on-off valve 7, the supply of the purge gas to the secondary side of the on-off valve 7 can be stopped. The on-off valve 7 is not particularly limited as long as it can select the open or closed state of the flow path. As with the on-off valve 5 described above, a solenoid valve can be used as the on-off valve 7.

The flow rate regulator (first flow rate regulator) 8 is located on the secondary side of the oxygen/moisture removal device 6 in the purge gas supply path L1, and regulates the flow rate of the purge gas into the sealed space 2A. The flow rate regulator 8 is not particularly limited as long as it is capable of regulating the flow rate of the purge gas. As the flow rate regulator 8, for example, a mass flow controller manufactured by Fujikin Co., Ltd. and the like can be mentioned.

As shown in FIG. 2, the on-off valve 5, the on-off valve 7, and the flow rate regulator 8, which are located in the purge gas supply path L1, are electrically connected to the control device 13 by wired or wireless signal lines. This allows control signals to be transmitted and received between the on-off valve 5, the on-off valve 7, and the flow rate regulator 8, and the control device 13 via the signal lines.

As shown in FIG. 1, the exhaust path L2 is an exhaust pipe that communicates with the sealed space 2A and exhausts the atmospheric gas in the sealed space 2A as exhaust gas to the outside of the cabinet 2. The connection position of the exhaust path L2 is near the upper side of the cabinet 2. As a result, the exhaust path L2 is located on the opposite side of the sealed space 2A to the outlets L1a and L1b arranged in the sealed space 2A, and thus convection of the atmospheric gas in the sealed space 2A from the lower side to the upper side is promoted.

The oxygen concentration measuring device 9 is located in the exhaust path L2, and measures the oxygen concentration in the atmospheric gas exhausted from the sealed space 2A to the exhaust path L2. In other words, the oxygen concentration measuring device 9 indirectly measures the oxygen concentration in the sealed space 2A by measuring the oxygen concentration in the atmospheric gas exhausted from the sealed space 2A to the exhaust path L2.

The oxygen concentration measuring device 9 is not particularly limited as long as it is capable of measuring the oxygen concentration. An example of the oxygen concentration measuring device 9 is an oxygen concentration measuring device manufactured by Michell.

The moisture concentration measuring device 10 is located in the exhaust path L2 and measures the moisture concentration in the atmospheric gas exhausted from the sealed space 2A to the exhaust path L2. In other words, the moisture concentration measuring device 10 indirectly measures the moisture concentration in the sealed space 2A by measuring the moisture concentration in the atmospheric gas exhausted from the sealed space 2A to the exhaust path L2.

The moisture concentration measuring device 10 is not particularly limited as long as it is capable of measuring the moisture concentration. An example of the moisture concentration measuring device 10 is a dew point measuring device manufactured by Michell.

As shown in FIG. 2, the oxygen concentration measuring device 9 and the moisture concentration measuring device 10 are connected to the control device 13 by a wired or wireless signal line. This allows measurement values of the oxygen concentration and the moisture concentration in the sealed space 2A to be transmitted and received as electrical signals between the oxygen concentration measuring device 9 and the moisture concentration measuring device 10 and the control device 13.

As shown in FIG. 1, the bypass path L3 is a gas supply pipe that branches off from the purge gas supply path L1 at the branch point P on the primary side of the on-off valve 5 and merges with the purge gas supply path L1 at the junction Q on the secondary side of the flow rate regulator 8. In other words, the bypass path L3 is a gas supply pipe that supplies the raw air flowing through the purge gas supply path L1 to the secondary side of the oxygen/moisture removal device 6 by bypassing the oxygen/moisture removal device 6. The bypass path L3 allows the purge gas containing the raw air to be supplied to the sealed space 2A inside the cabinet 2.

In the bypass path L3, on the secondary side of the branch point P and on the primary side of the junction point Q, the on-off valve (second on-off valve) 11 and the flow rate regulator (second flow rate regulator) 12 are located in this order.

The on-off valve 11 is located in the bypass path L3 and selects an open or closed state of the flow path of the bypass path L3. By opening the on-off valve 11, the raw air can be supplied to the secondary side of the on-off valve 11. On the other hand, by closing the on-off valve 11, the supply of the raw air to the secondary side of the on-off valve 11 can be stopped. The on-off valve 11 is not particularly limited as long as it can select the open or closed state of the flow path. For example, a solenoid valve can be used as the on-off valve 11.

The flow rate regulator 12 is located in the bypass path L3 and regulates the flow rate of the raw air supplied to the purge gas supply path L1 via the bypass path L3. In other words, the flow rate regulator 12 regulates the flow rate of the purge gas to the sealed space 2A. The flow rate regulator 12 is not particularly limited as long as it can regulate the flow rate of the raw air. As the flow rate regulator 12, for example, a mass flow controller manufactured by Fujikin Co., Ltd. and the like can be mentioned.

As shown in FIG. 2, the on-off valve 11 and the flow rate regulator 12, which are located in the bypass path L3, are electrically connected to the control device 13 by wired or wireless signal lines. This allows control signals to be transmitted and received between the on-off valve 11 and the flow rate regulator 12 and the control device 13 via signal lines.

As shown in FIG. 1, in the storage 1 of the present embodiment, the purge gas introduced into the sealed space 2A in the cabinet 2 preferably has a low moisture content and is dry from the viewpoint of removing moisture contained in the raw powder. Specifically, the dew point of the purge gas is preferably −50° C. or less, and more preferably −60° C. or less. As the purge gas used in the storage 1 of the present embodiment, nitrogen gas with a dew point of −50° C. or less is preferable.

As shown in FIG. 2, the control device 13 is electrically connected to the heater 3, the temperature measuring device 4, the on-off valve 5, the on-off valve 7, the flow rate regulator 8, the oxygen concentration measuring device 9, the moisture concentration measuring device 10, the on-off valve 11, and the flow rate regulator 12 by wired or wireless signal lines. This allows measured values of the temperature, the oxygen concentration, and the moisture concentration of the sealed space 2A to be transmitted and received as electrical signals between the control device 13 and the temperature measuring device 4, the oxygen concentration measuring device 9, and the moisture concentration measuring device 10. In addition, control signals can be transmitted and received as electrical signals between the control device 13 and the heater 3, the on-off valve 5, the on-off valve 7, the flow rate regulator 8, the on-off valve 11, and the flow rate regulator 12.

The control device 13 is not particularly limited as long as it has the above-mentioned transmission and reception functions. The control device 13 may be a programmable logic controller (PLC), a PC, a tablet, or the like.

As described above, the storage 1 of the present embodiment can control the flow rate and the composition (oxygen concentration) of the purge gas supplied to the sealed space 2A in accordance with the measured values of the oxygen concentration and the moisture concentration in the sealed space 2A.

Furthermore, the storage 1 of the present embodiment can control the output of the beater 3 located in the sealed space 2A in accordance with the measured values of the moisture concentration and the temperature of the sealed space 2A.

Method for Storing Powder Material for Metal 3D Printer

Figure 3:
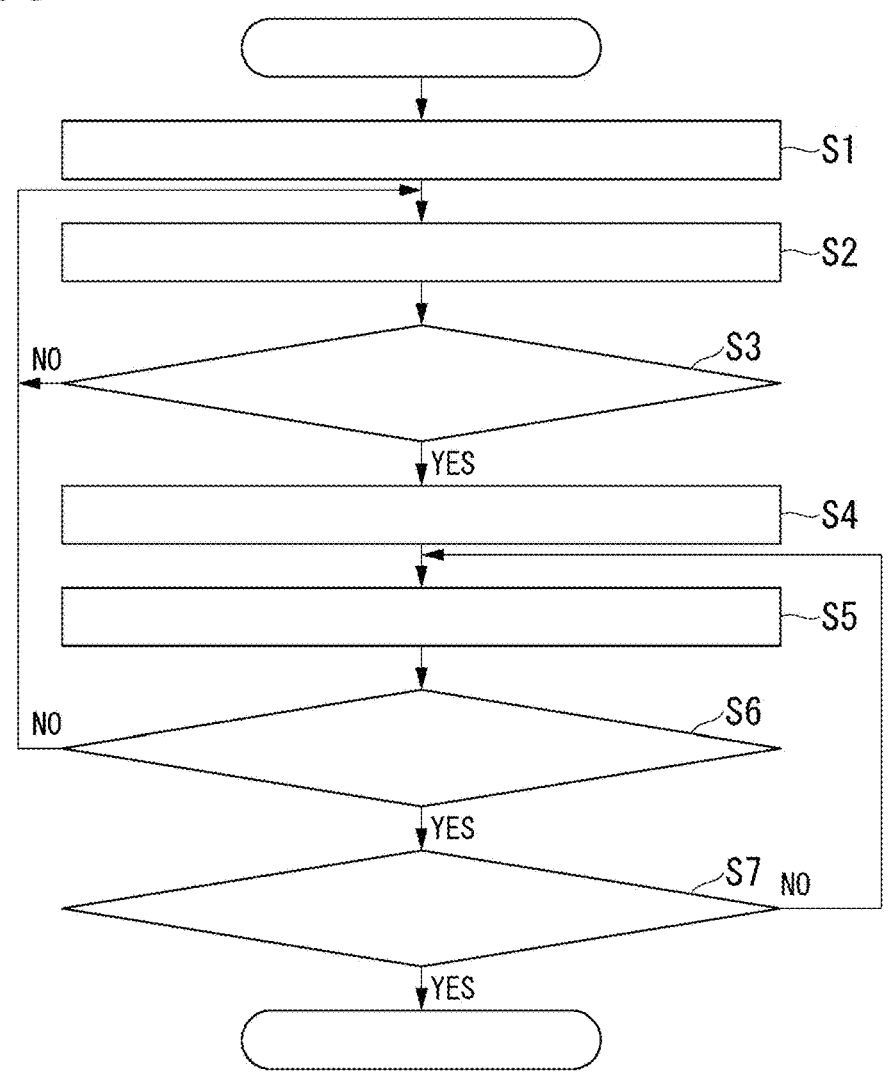
FIG. 3 is a flow chart showing an embodiment of a method for storing powder material for a metal 3D printer according to the present invention.

Next, a method for storing powder material for a metal 3D printer, which is an embodiment of the present invention, will be described. FIG. 3 is a flow chart showing an embodiment of a method for storing powder material for a metal 3D printer according to the present invention.

The method for storing powder material for a metal 3D printer of the present embodiment (hereinafter sometimes simply referred to as "storing method") is performed using the storage 1 described above.

In the storing method of the present embodiment, one or more storage containers S containing the raw powder are placed in the sealed space 2A inside the cabinet 2, and the purge gas made from air as a raw material and obtained by removing oxygen and moisture from the air is supplied at a required flow rate from the purge gas supply path L1 to the sealed space 2A.

Below, the storing method of the present embodiment will be specifically described with reference to FIG. 3.

As shown in FIG. 3, operation of the storage 1 is started (START).

First, as shown in step S1, the raw powder is stored or removed.

Specifically, to store the raw powder, the door of the cabinet 2 is opened and one or more storage containers S are placed on the mounting surface of any of the shelves 2B. On the other hand, to remove the raw powder, the door of the cabinet 2 is opened and one or more storage containers S are placed on any of the shelves 2B are removed from the storage 1.

In addition, if raw powder is already stored, when the door of the cabinet 2 is opened, the purge gas in the sealed space 2A may flow out, which may cause oxygen deficiency for the worker. In this case, it is preferable to open the on-off valve 11 of the bypass path L3 and control the flow rate regulator 12 to supply the raw air to the purge gas supply path L1 and to supply it as purge gas to the sealed space 2A of the storage 1. In this way, when the storage 1 is opened, the raw air also flows out together with the purge gas, which can prevent oxygen deficiency for the worker.

Next, as shown in step S2, the purge gas is supplied to the sealed space 2A of the storage 1.

Specifically, after the door of the cabinet 2 is closed, the on-off valves 5 and 7 are opened and the on-off valve 11 is closed, and the purge gas is supplied to the sealed space 2A from the purge gas supply path L1. In addition, the purge gas is supplied while controlling the supply amount using the flow rate regulator 8. At the same time, the atmospheric gas in the sealed space 2A is exhausted to the outside of the cabinet 2 as exhaust gas from the exhaust path L2.

Next, as shown in step S3, it is determined whether the moisture concentration and the oxygen concentration in the sealed space 2A of the storage 1 are below required thresholds.

Specifically, when the atmospheric gas is exhausted from the exhaust path L2, the oxygen concentration in the atmospheric gas is measured by the oxygen concentration measuring device 9, and the moisture concentration in the atmospheric gas is measured by the moisture concentration measuring device 10, and it is determined whether the moisture concentration and the oxygen concentration in the sealed space 2A are below required thresholds.

If the result of the determination is that either the moisture concentration or the oxygen concentration in the sealed space 2A is greater than the required threshold value (NO judgement), the process returns to step S2, and the amount of the purge gas supplied is controlled.

Here, in step S2, the amount of the purge gas supplied may be changed according to the measured moisture concentration value. For example, if the moisture concentration in the sealed space 2A is higher than the required threshold value, it is preferable to set the flow rate of the purge gas to a high flow rate that can completely replace the atmospheric gas in the sealed space 2A of the storage 1 within 1 to 60 minutes. By supplying a high flow rate of the purge gas, moisture present in the sealed space 2A of the storage 1, particularly moisture adsorbed on the surface of the raw powder, can be quickly removed.

In this way, by controlling the flow rate and the composition ratio (oxygen concentration) of the purge gas supplied to the sealed space 2A of the storage 1 in accordance with the measured value of the impurity concentration in the sealed space 2A, the atmosphere in the sealed space 2A of the storage 1 can be quickly brought to the desired state.

The oxygen concentration in the sealed space 2A may be 6% by volume or less, preferably 3% by volume or less, and more preferably 1% by volume or less. By keeping the oxygen concentration in the sealed space 2A at 3% by volume or less, oxidation of the raw powder during storage can be suppressed.

The moisture concentration in the sealed space 2A may be equal to or lower than the dew point temperature of −40° C., preferably equal to or lower than −50° C., and more preferably equal to or lower than −60° C. By making the moisture concentration in the sealed space 2A equal to or lower than the dew point temperature of −40° C., it is possible to obtain an effect of removing moisture from the raw powder that has absorbed moisture and an effect of suppressing moisture absorption.

On the other hand, if the result of the judgment in step S3 is that the measured values of both the moisture concentration and the oxygen concentration in the sealed space 2A are equal to or lower than the required threshold value (YES judgment), the process proceeds to step S4, where the supply of the purge gas is stopped. Specifically, the on-off valves 5, 7, and 11 are closed. This makes it possible to reduce energy consumption according to the storing method of the present embodiment. In addition, since the load on the oxygen/moisture removal device 6 can be reduced, the life of the oxygen/moisture removal device 6 can be extended.

Next, as shown in step S5, after a required time has elapsed, the purge gas is supplied to the sealed space 2A. At the same time, the atmospheric gas in the sealed space 2A is exhausted to the outside of the cabinet 2 through the exhaust path L2 as exhaust gas.

Here, the supply amount of the purge gas is preferably set to a flow rate that can completely replace the atmospheric gas in the sealed space 2A of the storage 1 within 1 to 60 minutes. From the viewpoint of measuring the oxygen concentration and the moisture concentration in the storage 1 in a short period of time, it is more preferable to set the flow rate that can completely replace the atmospheric gas in the sealed space 2A of the storage 1 within 1 to 10 minutes.

In addition, it is preferable that the purge gas be supplied to the sealed space 2A from the plurality of outlets L1a and L1b that open at the bottom of the sealed space 2A. This allows the sealed space 2A of the storage 1 to be agitated over a wide range, so that stable measurement values of the moisture concentration and the oxygen concentration can be obtained in step S6 described later.

Next, as shown in step S6, it is judged whether the moisture concentration and the oxygen concentration in the sealed space 2A of the storage 1 are below required thresholds.

Specifically, as in step S3 described above, when atmospheric gas is exhausted from the exhaust path L2, the oxygen concentration in the atmospheric gas is measured by the oxygen concentration measuring device 9, and the moisture concentration in the atmospheric gas is measured by the moisture concentration measuring device 10, and it is judged whether the moisture concentration and the oxygen concentration in sealed space 2A are below required thresholds.

If the judgment result indicates that either the moisture concentration or the oxygen concentration in the sealed space 2A is greater than the required threshold value (NO judgment), the process returns to step S2, and the supply of the purge gas is resumed.

On the other hand, if the judgment result indicates that both the measured values of the moisture concentration and the oxygen concentration in the sealed space 2A are equal to or lower than the required threshold value (YES judgment), the supply of the purge gas is stopped. Specifically, the on-off valves 5, 7, and 11 are closed. This reduces energy consumption. In addition, since the load on the oxygen/moisture removal device 6 is reduced, the life of the oxygen/moisture removal device 6 can be extended.

Next, as shown in step S7, a judgment is made as to whether or not to stop the operation of the storage 1.

If the judgment result indicates that the operation of the storage 1 is to be continued without being stopped (NO judgment), the process returns to step S5, and after the supply of the purge gas has been stopped and a required time has elapsed, the purge gas is again supplied to the sealed space 2A, and the moisture concentration and the oxygen concentration in the sealed space 2A are measured.

According to the storing method of the present embodiment, when the impurity concentration in the sealed space 2A of the storage 1 becomes equal to or lower than a required threshold, the supply of the purge gas is stopped, and then the purge gas is supplied to the sealed space 2A every required time, and the moisture concentration and the oxygen concentration in the sealed space 2A are measured, thereby reducing the amount of energy consumed by the storage 1 and maintaining a suitable storage environment for the raw powder. In addition, since the load on the oxygen/moisture removal device 6 can be reduced, the life of the oxygen/moisture removal device 6 can be extended.

Furthermore, according to the storing method of the present embodiment, both the oxygen concentration measuring device 9 and the moisture concentration measuring device 10 are positioned in the exhaust path L2. Therefore, when the supply of the purge gas to the sealed space 2A is stopped, the exhaust gas does not flow, and there is a risk that the impurity concentration in the sealed space 2A of the storage 1 cannot be accurately measured. However, by supplying the purge gas to the sealed space 2A every time a required time has elapsed, the impurity concentration in the sealed space 2A of the storage 1 can be accurately measured.

In addition, the interval for supplying the purge gas to measure the impurity concentration inside the storage 1 after the supply of the purge gas is stopped is not particularly limited, and can be selected appropriately depending on the sealing performance and volume of the storage 1.

On the other hand, if the judgment result in step S7 indicates that the operation of the storage 1 should be stopped (YES judgment), the operation of the storage 1 is ended (END).

Modified Embodiment 1

In the storing method of the present embodiment, when supplying the purge gas in step S2 described above, the purge gas may be supplied while heating the sealed space 2A of the storage 1 only while the moisture concentration is higher than a required threshold value.

Heating of the sealed space 2A of the storage 1 by the heater 3 is stopped when the moisture concentration falls below a required threshold value.

In addition, from the viewpoint of maintaining the storage environment of the raw powder, the sealed space 2A of the storage 1 may be heated by the heater 3 as necessary to maintain the temperature of the sealed space 2A of the storage 1 during the above-mentioned steps S5 to S7.

According to modified embodiment 1 of the storing method of the present embodiment, when the purge gas is supplied in step S2, the purge gas is supplied while the sealed space 2A of the storage 1 is heated only while the moisture concentration is higher than a required threshold, thereby promoting desorption and removal of moisture from the raw powder.

In addition, when the purge gas is supplied in step S2, if the moisture concentration is equal to or lower than the required threshold, the output of the heater 3 can be reduced, thereby reducing energy consumption when storing the raw powder.

As described above, according to the storage 1 and the storing method of the present embodiment, since a purge gas made of air is used, a storage environment suitable for powder material for a metal 3D printer can be provided without being restricted by the installation location. In particular, even if a utility facility for supplying inert gas cannot be provided due to regulations of the High Pressure Gas Safety Act, a storage environment suitable for powder material for a metal 3D printer can be provided.

Furthermore, according to the storage 1 and the storing method of the present embodiment, the raw powder can be stored under an optimal atmosphere, so that the quality of the raw powder used in the metal 3D printer can be maintained, which contributes to maintaining the performance of the molded object.

According to storage 1 and the storing method of the present embodiment, the raw powder can be stored in an optimal atmosphere, so oxidation of the raw powder can be suppressed. This makes it possible to reduce the amount of raw powder that is wasted. Furthermore, according to the storage 1 and the storing method of the present embodiment, storing the raw powder in the storage 1 makes it possible to dry raw powder that has absorbed moisture. This contributes to maintaining the performance of objects molded using a metal 3D printer.

According to the storage 1 and the storing method of the present embodiment, the flow rate of the purge gas can be controlled to optimize the supply amount of the purge gas, so that the amount of the purge gas used can be reduced. In addition, since the purge gas which is made from air, is used, an inert gas supply source such as nitrogen gas or argon gas is not required, so that the running cost for storing the raw powder can be reduced.

The technical scope of the present invention is not limited to the above-mentioned embodiments, and various modifications can be made without departing from the spirit of the present invention. For example, according to the storage 1 of the above-mentioned embodiment, the on-off valves 5 and 7 are provided on the primary side and secondary side of the oxygen/moisture removal device 6, as an example, but the present invention is not limited to this embodiment. For example, as shown in FIG. 4, the storage 21 may be configured such that the exhaust path LA branches off from a branch point R of the purge gas supply path L1 on the secondary side of the oxygen/moisture removal device 6 and the primary side of the on-off valve 7.

In the case of the storage 1 of the above embodiment, when the supply of the purge gas is stopped in step S4 described above, gas flows out of an exhaust path (not shown) that exhausts gas containing a large amount of oxygen and moisture from the oxygen/moisture removal device 6 (gas separation membrane module), causing a decrease in pressure in the oxygen/moisture removal device 6 and may result in air being drawn into the oxygen/moisture removal device 6. As a result, when the supply of the purge gas is resumed, purge gas with a high oxygen concentration may be supplied into the storage 21.

Figure 4:
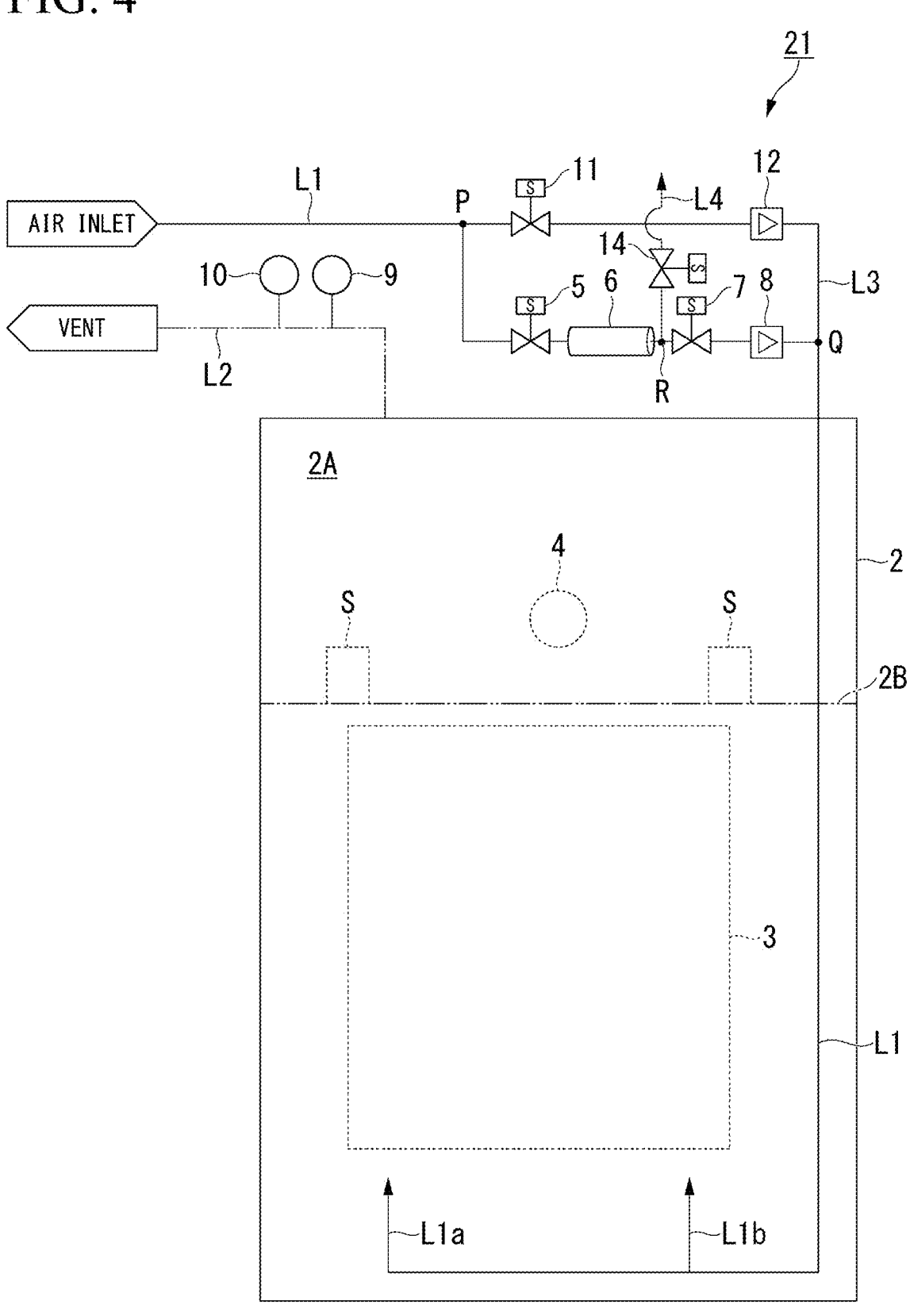
FIG. 4 is a schematic diagram showing a modified embodiment of the configuration of a storage for powder material for a metal 3D printer according to the present invention.

According to the storage 21 shown in FIG. 4, since it is provided with an exhaust path L4 having an on-off valve 14 on the secondary side of the oxygen/moisture removal device 6, when the supply of the purge gas is stopped in step S4 described above, the on-off valve 7 can be closed and the on-off valve 14 can be opened. This makes it possible to exhaust the purge gas derived from the oxygen/moisture removal device 6 from the exhaust path LA for a certain period of time and purge in order to prevent air from being drawn into the oxygen/moisture removal device 6. Therefore, according to the storage 21, when the supply of the purge gas is resumed, only clean purge gas can be supplied into the storage 21.

In addition, in the storage 1 of the present embodiment described above, an embodiment in which the heater 3 is provided as a means for heating the sealed space 2A in the cabinet 2, and when the purge gas is supplied, the purge gas is supplied while being blown onto the surface of the heater 3 is explained as an example. However, the present embodiment is not limited to this embodiment. For example, the purge gas supply path L1 may have a heater for heating the purge gas. Also, the sealed space 2A in the cabinet 2 may be heated by supplying a high-temperature purge gas, and the heater 3 may keep the sealed space 2A warm.

In addition, in the storage 1 of the present embodiment described above, the case where clean dry air (CDA) is used as raw air of the purge gas is described as an example, but is not limited thereto. For example, if there is no clean dry air supply equipment in the installation environment of the storage 1, the purge gas supply path L1 may be configured to be provided with an air compressor that compresses and supplies the raw air, a filter that removes particles in the air, and a moisture remover that removes moisture in the air.

In addition, in the storage 1 of the present embodiment described above, a configuration in which one oxygen/moisture removal device 6 is located in the purge gas supply path L1 as a purge gas generating device has been described as an example, but the present invention is not limited to this embodiment. For example, the purge gas supply path L1 may be branched into two or more paths, and the oxygen/moisture removal device 6 may be located in each of the branched paths. By providing a plurality of oxygen/moisture removal devices in parallel in this way, when the function of the oxygen/moisture removal device 6 in use deteriorates, the storage 1 can be operated continuously by switching to the spare oxygen/moisture removal device 6.

In addition, in the storage 1 of the present embodiment described above, an embodiment in which the bypass path L3 capable of supplying the raw air to the sealed space 2A of the storage 1 as a part of the purge gas is branched off from the purge gas supply path L1 and then merges again with the purge gas supply path L1 is explained as an example, but is not limited thereto. For example, the bypass path L3 branches off from the purge gas supply path L1 and then directly connects to the sealed space 2A of the storage 1 without merging with the purge gas supply path L1. Furthermore, the bypass path L3 may not be branched off from the purge gas supply path L1, but may be a path that is parallel to the purge gas supply path L1 from the beginning.

In the storage 1 of the present embodiment, the oxygen concentration measuring device 9 and the moisture concentration measuring device 10 are located in the exhaust path L2 as an example. However, the oxygen concentration measuring device 9 and the moisture concentration measuring device 10 may be located in the sealed space 2A of the storage 1.

Also, in the storage 1 of the present embodiment described above, a configuration in which the function of transmitting and receiving measurement values and control signals is concentrated in the control device 13 has been described as an example, but a configuration in which the function is divided into two or more elements or locations may also be used.

Furthermore, in the storage 1 of the present embodiment, if the heater 3, the on-off valve 5, the on-off valve 7, the flow rate regulator 8, the on-off valve 11, and the flow rate regulator 12 have the function of directly transmitting and receiving signals between the temperature measuring device 4, the oxygen concentration measuring device 9, and the moisture concentration measuring device 10, a configuration in which the control device 13 is omitted may also be used.

EXPLANATION OF SYMBOLS 1 storage for powder material for a metal 3D printer (storage)
2 cabinet (storage main body)
2A sealed space
3 heater
4 temperature measuring device
5 on-off valve (first on-off valve)
6 oxygen/moisture removal device
7 on-off valve (third on-off valve)
8 flow rate regulator (first flow rate regulator)
9 oxygen concentration measuring device
10 moisture concentration measuring device
11 on-off valve (second on-off valve)
12 flow rate regulator (second flow rate regulator)
L1 purge gas supply path
L2 exhaust path
L3 bypass path
L4 exhaust path
S storage container

The invention claimed is:

1. A storage for powder material for a metal 3D printer, comprising:
    a storage main body having a sealed space inside and capable of placing one or more storage containers for storing powder material for a metal 3D printer in the sealed space;
    a purge gas supply path for supplying a purge gas made from air to the sealed space;
    an oxygen/moisture removal device for removing oxygen and moisture from the air which is located in the purge gas supply path;
    a first on-off valve located on a primary side of the oxygen/moisture removal device in the purge gas supply path;
    a first flow rate regulator located on a secondary side of the oxygen/moisture removal device in the purge gas supply path;
    a bypass path branching off from the purge gas supply path on a primary side of the first on-off valve and merging with the purge gas supply path on a secondary side of the first flow rate regulator;
    a second on-off valve located in the bypass path;
    a second flow rate regulator located in the bypass path;
    an oxygen concentration measuring device measuring an oxygen concentration in the sealed space;
    a moisture concentration measuring device measuring a moisture concentration in the sealed space; and
    a control device configured to transmit and receive signals to and from the first on-off valve, the first flow rate regulator, the second on-off valve, the second flow rate regulator, the oxygen concentration measuring device, and the moisture concentration measuring device.

2. A storage for powder material for a metal 3D printer, comprising:

a storage main body having a sealed space inside and capable of placing one or more storage containers for storing powder material for a metal 3D printer in the sealed space;

a purge gas supply path for supplying a purge gas made from air to the sealed space;

an oxygen/moisture removal device for removing oxygen and moisture from the air which is located in the purge gas supply path;

an on-off valve located on a secondary side of the oxygen/moisture removal device in the purge gas supply path, and an exhaust path branching off from the purge gas supply path on the secondary side of the oxygen/moisture removal device and a primary side of the on-off valve, and the exhaust path being associated with another on-off valve.

3. A storage for powder material for a metal 3D printer, comprising:

a storage main body having a sealed space inside and capable of placing one or more storage containers for storing powder material for a metal 3D printer in the sealed space;

a purge gas supply path for supplying a purge gas made from air to the sealed space;

an oxygen/moisture removal device for removing oxygen and moisture from the air which is located in the purge gas supply path;

a third on-off valve located on a secondary side of the oxygen/moisture removal device in the purge gas supply path, an exhaust path branching off from the purge gas supply path on the secondary side of the oxygen/moisture removal device and a primary side of the third on-off valve;

a first on-off valve located on a primary side of the oxygen/moisture removal device in the purge gas supply path;

a first flow rate regulator located on the secondary side of the oxygen/moisture removal device in the purge gas supply path;

a bypass path branching off from the purge gas supply path on a primary side of the first on-off valve and merging with the purge gas supply path on a secondary side of the first flow rate regulator;

a second on-off valve located in the bypass path;

a second flow rate regulator located in the bypass path;

an oxygen concentration measuring device measuring an oxygen concentration in the sealed space;

a moisture concentration measuring device measuring a moisture concentration in the sealed space; and a control device configured to transmit and receive signals to and from the first on-off valve, the first flow rate regulator, the second on-off valve, the second flow rate regulator, the oxygen concentration measuring device, and the moisture concentration measuring device.

4. The storage for powder material for a metal 3D printer according to claim 1, wherein the oxygen/moisture removal device is a gas separation membrane or a filled cylinder filled with a gas adsorbent.

5. The storage for powder material for a metal 3D printer according to claim 1, wherein the storage further comprises:

a heater for heating the sealed space, and a temperature measuring device for measuring a temperature of the sealed space.

6. The storage for powder material for a metal 3D printer according to claim 5, wherein an outlet of the purge gas supply path opens at the bottom of the sealed space.

7. The storage for powder material for a metal 3D printer according to claim 1, wherein the storage further comprises an exhaust path for exhausting atmospheric gas in the sealed space to the outside of the storage main body as exhaust gas, and wherein at least one of the oxygen concentration measuring device and the moisture concentration measuring device are positioned in the exhaust path.

8. The storage for powder material for a metal 3D printer according to claim 2, wherein the oxygen/moisture removal device is a gas separation membrane or a filled cylinder filled with a gas adsorbent.

9. The storage for powder material for a metal 3D printer according to claim 2, wherein the storage further comprises:

a heater for heating the sealed space, and a temperature measuring device for measuring a temperature of the sealed space.

10. The storage for powder material for a metal 3D printer according to claim 9, wherein an outlet of the purge gas supply path opens at the bottom of the sealed space.

11. The storage for powder material for a metal 3D printer according to claim 3, wherein the oxygen/moisture removal device is a gas separation membrane or a filled cylinder filled with a gas adsorbent.

12. The storage for powder material for a metal 3D printer according to claim 3, wherein the storage further comprises:

a heater for heating the sealed space, and a temperature measuring device for measuring a temperature of the sealed space.

13. The storage for powder material for a metal 3D printer according to claim 12, wherein an outlet of the purge gas supply path opens at the bottom of the sealed space.

14. The storage for powder material for a metal 3D printer according to claim 3, wherein the storage further comprises an exhaust path for exhausting atmospheric gas in the sealed space to the outside of the storage main body as exhaust gas, and wherein at least one of the oxygen concentration measuring device and the moisture concentration measuring device are positioned in the exhaust path.

15. A method for storing powder material for a metal 3D printer using the storage for powder material for a metal 3D printer according to claim 1, comprising:

placing one or more storage containers for storing powder material for a metal 3D printer in the sealed space, and supplying a purge gas, which is made from air and obtained by removing oxygen from the air, to the sealed space.

16. The method for storing powder material for a metal 3D printer according to claim 15, wherein the supply of the purge gas is stopped after the moisture concentration and the oxygen concentration in the sealed space fall below required threshold values.

17. The method for storing powder material for a metal 3D printer according to claim 16, wherein after the supply of the purge gas is stopped, the purge gas is supplied to the sealed space every required time, and the moisture concentration and the oxygen concentration in the sealed space are measured.

18. The method for storing powder material for a metal 3D printer according to claim 17, wherein the supply of the purge gas is resumed when at least one of the moisture concentration and the oxygen concentration in the sealed space exceeds a threshold value.

19. The method for storing powder material for a metal 3D printer according to claim 15, wherein a temperature of the sealed space is set to a required temperature.

20. The method for storing powder material for a metal 3D printer according to claim 15, wherein the oxygen concentration in the sealed space is maintained at 3% by volume or less, and a dew point temperature of the sealed space is maintained at −40° C. or less.

* * * * *